United States Patent [19]
Berger

[11] Patent Number: 4,718,833
[45] Date of Patent: Jan. 12, 1988

[54] ELECTROPNEUMATIC CONVERTER
[75] Inventor: Henri Berger, Argenteuil, France
[73] Assignee: Societe d'Applications Generales d'Electricite, et de Mecanique SAGEM, Paris, France
[21] Appl. No.: 851,519
[22] Filed: Apr. 14, 1986
[30] Foreign Application Priority Data
Apr. 16, 1985 [FR] France ................ 85 05697
[51] Int. Cl.4 .......... F04B 49/00; F04B 9/08; F04B 17/06
[52] U.S. Cl. ............... 417/16; 417/46; 417/383; 417/390; 623/3
[58] Field of Search .......... 417/16, 45, 46, 383, 417/390; 623/3
[56] References Cited
U.S. PATENT DOCUMENTS
2,621,608 12/1952 McIntyre .................. 417/46
3,496,879 2/1970 Brandes .................. 417/46
4,381,567 5/1983 Robinson ................. 128/1 D
4,382,799 5/1983 Isaacson .................. 623/3
4,611,578 9/1986 Heimis .................... 417/383

FOREIGN PATENT DOCUMENTS
2123089 1/1984 United Kingdom .

Primary Examiner—William L. Freeh
Attorney, Agent, or Firm—Stevens, Davis, Miller & Mosher

[57] ABSTRACT

An electropneumatic converter is provided comprising a gear pump. The two toothed wheels are driven by two electric motors rotating at high speed in opposite directions. The control circuits for each of the motors are independent and a single motor may drive the pump permanently.

The converter is used, for example in an activator for a cardiac module or artificial heart.

4 Claims, 2 Drawing Figures

ELECTROPNEUMATIC CONVERTER

BACKGROUND OF THE INVENTION

1. Field of the Invention

The present invention relates to an electropneumatic converter comprising a displacement pump driven by at least one electric motor.

Such a converter is used, for example, in the biomedical field for the pneumatic control of a cardiac module, or artificial heart.

An artificial heart is formed mainly of two ventricle, each comprising a flexible bag or blood bag whose deformation for aspirating or delivering the blood is controlled by the deformation of a gas bag, for example an air or nitrogen bag. Each of the two gas bags, corresponding to each of the two ventricles, is connected periodically through a distributor to the inlet and to the outlet of the pump of an electropneumatic converter of the above type.

Such converters are already known, whose volume is however never less than 10 cubic decimeters or so, which makes it impossible to implant them in a patient. Serious disadvantages occur for the patient in whom a cardiac module has been implanted.

2. Description of the Prior Art

To overcome these drawbacks, a displacement pump is sought which, for a given delivery rate, has reduced volume. A pump is known offering this advantage, described in the British patent application published under the No. 2 123 089. It is a gear displacement pump with two gear wheels each of which is driven by its own electric motor, in which two independent electronic circuits are provided for controlling the motors, connected to computing means adapted for controlling the motors so that the teeth of the first toothed wheel are always in contact with the teeth of the second toothed wheel.

In this known pump, the reduction of volume, for a given delivery rate, is obtained because, since none of the toothed wheels is subjected to a drive torque by the other toothed wheel, as in a gear pump with a single motor, they may be dimensioned for withstanding only the load due to the pressure difference of the pumped fluid, which results in a reduction of the size of the toothed wheels.

The result is that if such a pump is used in a converter for the pneumatic control of an artificial heart, any breakdown occurring in one of the motors, or in one of the electronic circuits controlling the motors, is fatal for the converter since, as soon as a toothed wheel ceases to be driven by its own motor, it is subjected to mechanical stresses for which it has not been provided.

The present invention aims at overcoming this drawback.

SUMMARY OF THE INVENTION

For this it provides an electropneumatic converter comprising a gear displacement pump having two toothed wheels each of which is driven by its own electric motor, in which two independent electronic circuits are provided for controlling the motors, connected to computing means adapted for controlling the motors so that the teeth of the first toothed wheel are always in contact with the teeth of the second toothed wheel, each toothed wheel and each electric motor are dimensioned so that each motor may drive the pump alone and permanently, a circuit is provided for checking the power supply current for each of the electronic control circuits, external signalling means are provided connected to the checking circuit, and opening means are provided, connected to the checking circuit, for opening the power supply connection of each of the electronic control circuits, should the power supply current depart from a given range.

In the converter of the invention, should one of the two motors or an electronic component belonging to one of the two circuits fail, the other motor, or the other circuit allows the converter of the invention to continue operating.

The corresponding measuring circuit detects the variation of the power supply current consumed by the circuit, which results in external signalling and making the defective motor or circuit inoperative by opening the power supply connection. Thus, the patient or the people looking after him are warned of a malfunction and, while waiting for the repair to be carried out, any consumption of current by the defective motor or circuit is avoided, normal operation of the converter being provided by a single electronic control circuit and a single motor, whose dimensioning is provided accordingly. The safety of the patient is thus ensured and any useless consumption of current from the implanted battery is avoided.

In the converter of the invention, dimensioning of the toothed wheels, provided so that they can resist during the time when, with one motor broken down, the pump is driven by a single motor, does not cause a critical increase in the volume of the pump, which may remain of a reduced size. In fact, the loss of power of the pump related to a reduction of its dimensions may be here accomodated by an increase in the rotational speed which, because of the type of pump used, causes no gyroscopic effect tending to oppose the movement of the converter, which would be intolerable for the patient in whose body such a converter might be implanted.

Advantageously, the electric motors and the displacement pump rotate on hydrodynamic bearings.

Again advantageously, the electric motors are brushless DC motors.

BRIEF DESCRIPTION OF THE DRAWINGS

The invention will be better understood from the following description of the preferred embodiment of the converter of the invention, with reference to the accompanying drawings in which.

DESCRIPTION OF THE PREFERRED EMBODIMENTS

Figure 1:
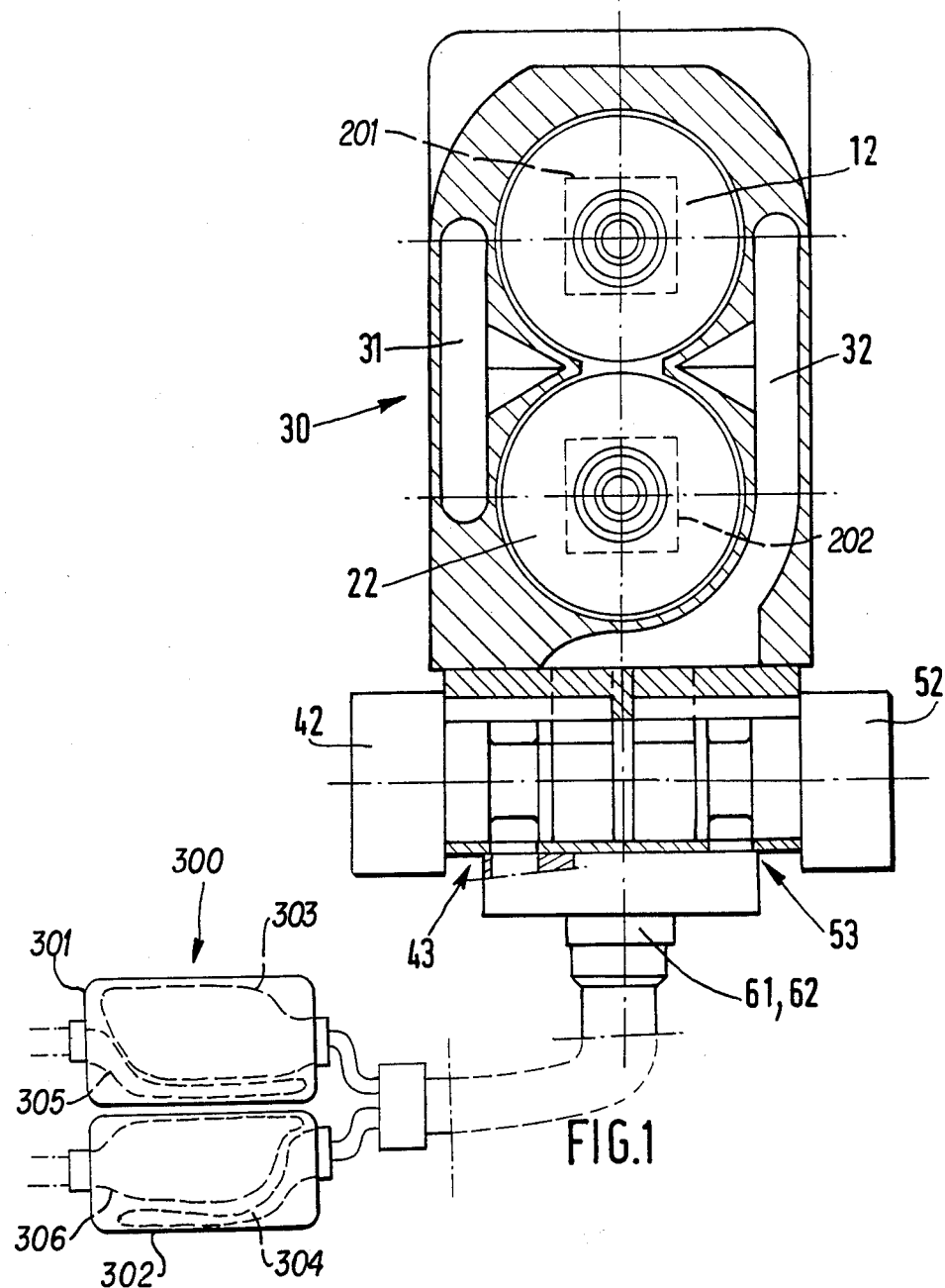
FIG. 1 shows a view in partial section of the mechanical part of a pneumatic activator comprising the electropneumatic converter of the invention.

With reference to FIG. 1, a pneumatic activator, implanted in the body of a patient, for the pneumatic control of a cardiac module, or artificial heart (not shown) also implanted in the body of the patient, to which it is connected by an assembly of two coaxial tubes 61 and 62 comprises an electropneumatic converter only the gear displacement pump 30, of conventional design, of which is shown and two rotary distributors also of conventional design, 43 and 53 connected to two motors 42 and 52, here stepper motors.

The output shafts of two electrically commutated direct current electric motors, i.e., brushless DC motors 12 and 22, here identical and rotating in hydrodynamic bearings 201 and 202, are respectively connected to the two toothed wheels of the gear of the pump 30.

The inlet pipe 31, and the outlet pipe 32 of pump 30 are connected to a first access duct and to a second access duct, respectively, of each rotary distributor 43 and 53.

A third access duct of the rotary distributor 53 is connected to the left ventricle 301 of the cardiac module 300 by a first coaxial tube 61.

A third access duct of the rotary distributor 43 is connected to the right ventricle 302 of the cardiac module 300 by a second coaxial tube 62.

Figure 2:
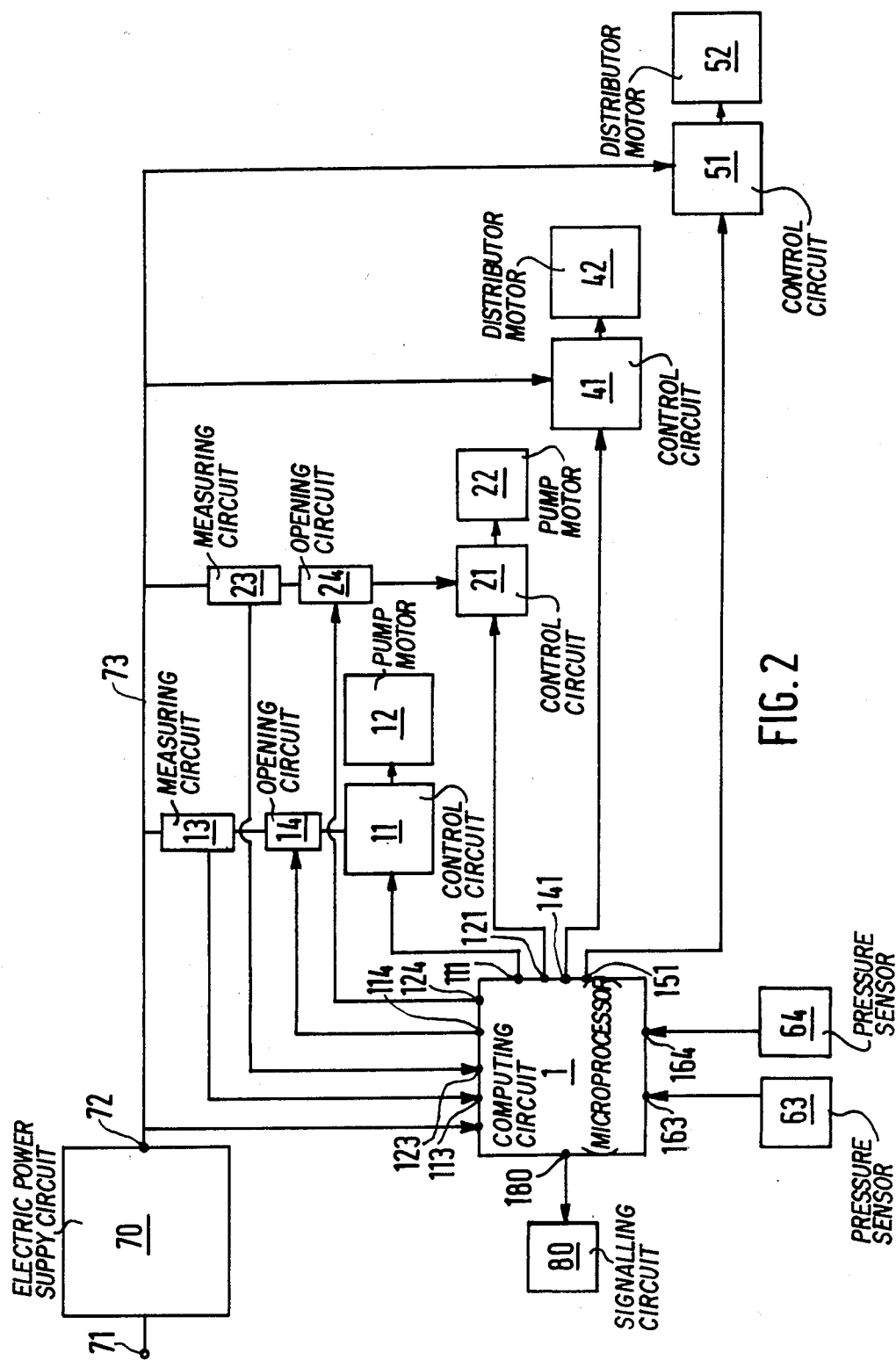
FIG. 2 shows a block diagram of the pneumatic activator of FIG. 1.

With reference to FIG. 2, a supply circuit 70 comprises, conventionally, a battery charger, a battery, a DC-DC converter, and a circuit for coupling to an external battery (not shown) between inputs external to the patient, only one of which 71 has been shown, and outputs, only one of which 72 has been shown for the sake of clarity.

One output 72 of the supply circuit 70 is connected, by a conductor 73, to the supply inputs of computing circuit, in the case in point a microprocessor 1, and two electronic circuits 41 and 51 for controlling the motors 42 and 52 respectively.

Conductor 73 is also connected to the supply input of an electronic circuit 11, respectively 21, for controlling the motor 12, respectively 22, through a measuring circuit 13, respectively 23, and an opening circuit 14, respectively 24, mounted in cascade with the measuring circuit 13, respectively 23.

The inputs of the electronic control circuits 11, 21, 41 and 51 are connected to four outputs 111, 121, 141 and 151 of the microprocessor 1.

Data outputs of the measuring circuits 13 and 23 are connectd to two inputs 113 and 123 of the microprocessor 1.

The inputs of the opening circuits 14 and 24 are connected to two outputs 114 and 124 of the microprocessor.

Two pressure sensors 63 and 64, placed in the third access ducts of the rotary distributors 43 and 53, respectively, connected to the right 302 and left 301 ventricles of the cardiac module 300, respectively, are connected to two inputs 163 and 164 of the microprocessor 1.

A signalling circuit 80, external to the body of the patient, comprising for example a light emitting diode, is connected to an output 180 of the microprocessor 1.

Electronic control circuits 11, 21, 41 and 51 are power amplifiers of conventional type for controlling electric motors.

The measuring circuit 13 comprises a low value resistor between the input connected to conductor 73 and the output connected to the opening circuit 14 and an analog-digital converter having one differential input whose two terminals are connected to two terminals of the resistor and whose digital output forms the data output of the measuring circuit 13. The measuring circuit 23 is identical to circuit 13.

The opening circuit 14 comprises a fuse between the input connected to the measuring circuit 13 and the output connected to the supply input of the electronic control circuit 11, and a thyristor whose gate forms the input of the opening circuit 14, its anode being connected to the output connected to the supply input of the electronic control circuit 11, and its cathode being connected to ground. The opening circuit 24 is identical to the opening circuit 14.

The assembly which has just been described, whose dimensions are fairly small so as to be compatible with implantation, operates in the following way.

The supply circuit 70 allows the whole of the circuits and the motors to be supplied with electric power, because of the electric energy which it has accumulated in the battery, or because of that which is permanently delivered thereto through the input 71, depending on the type of activity of the patient.

In normal operation, the microprocessor 1 drives circuits 11 and 21 and so motors 12 and 22 at high speed so as to obtain sufficient pneumatic power despite the reduced size. Microprocessor 1 is adapted so that each supplies about half of the total power to be supplied, taking into account what is required for the patient and the different yields, while however maintaining the power of one of the two motors slightly greater than that of the other, so that the teeth of the two toothed wheels are always in contact with each other, for correctly supplying the gas, here air.

The gyroscopic torque is therefore zero, since the two motors, rotating at high speed are identical and rotate in opposite directions. Thus the patient may move without gyroscopic torque opposing the corresponding movements of the converter.

The microprocessor 1 also drives the rotary distributors 43 and 53, through control circuits 41 and 51 and motors 42 and 52. Because of the pressure sensors 63 and 64, the control of these distributors may be made dependent thereon, and because of the stepper motors 42 and 52, control thereof may be progessive, which allows the air bag 304 of the right ventricle 302 and air bag 303 of the left ventricle 301 of the cardiac module to be placed progressively in communication with the inlet 31 or outlet 32 duct of pump 30, so as to provide gas aspiration and delivery in bags 303 and 304, so as to provide deformation of blood bags 305 and 304 and blood aspiration and delivery phases close to those of a living heart, and not prematurely fatiguing the valves of the artificial heart.

If a breakdown occurs, for example for motor 12, or for a component of the control circuit 11, the result is an abnormal variation of the supply current which flows through the measuring circuit 13. Microprocessor 1, which permanently compares the digital output data from the measuring circuit 13 with an upper threshold and with a lower threshold, which are not crossed during normal operation, then detects the deficiency.

In response, it sends signals to the output 180 and to the output 114. Thus, the sick person or the people attending him are warned because of circuit 80. The defective assembly is placed out of operation because of destruction of the fuse of the opening circuit 14, following the enabling of the thyristor, which opens then the power supply connection. The defective assembly thus no longer consumes electric power uselessly.

The remaining motor, in this case motor 22, suitably dimensioned then supplies to the assembly the necessary power and since it continues to drive the motor out of service, the gyroscopic torque continues to remain zero.

By way of example, in the described embodiment, each of the motors 12 and 22 may supply a nominal power of 6 W and, in normal operation, each motor supplies a power less than 3 W.

If it were necessary, it is possible to increase the operational safety of the assembly by providing two additional electronic control circuits, similar to circuits 41 and 51, for replacing one of these latter in the case of a breakdown. Measuring circuits may then be provided for circuits 41 and 51, similar to circuits 13 and 23 and opening circuits, similar to circuits 14 and 24, arranged comparably, for preventing circuit 41 from being provided with power uselessly, and circuit 51, in the case of a breakdown of one of these two, or of these two circuits.

It should, however be noted, that contrary to what happens for motor 22, for example, it is necessary, if it is desired to protect against a breakdown of motor 42, to provide a double thereof, for the two rotary distributors 43 and 53 work independently of each other. On the contrary, and in accordance with the invention, the use of two motors 12 and 22 for the gear pump 30 at the same time cancels out the gyroscopic torque and ensures safety in the case of breakdown without an increase of volume.

The signalling circuit 80 which has been described is disposed outside the body of the patient and it comprises a light emitting diode. It is also possible to provide a signalling circuit inside the body of the patient, having for example a sound signalling system such as a buzzer.

The application of the electropneumatic converter of the invention is not limited to the that which has just been described, for controlling a cardiac module. It may for example be used for any other biomedical application, implanted or not and generally in any application where it is useful to have a small volume electropneumatic converter, without gyroscopic torque, and offering great operational reliability.

What is claimed is:

1. An electropneumatic converter to be inserted between an electric power supply and at least two gas bags, said converter comprising an electrically driven pump having an input and an output; means for connecting periodically each of said bags to said input and said output to periodically aspirate and deliver gas in each of said bags; said pump comprising a gear displacement pump with two toothed wheels, a pair of electric motors for driving respective ones of said toothed wheels, two independent electronic circuits for controlling respective ones of said motors, a computing means connected to said electronic circuits, said toothed wheels having teeth which are always in contact with one another, each of said toothed wheels and each of said motors being adapted so that each of said motors may drive the pump alone and permanently; measuring means, connected to said computing means, for measuring a power supply current to each of said electronic circuits; external signalling means, connected to said computing means; opening means, connected to said computing means, for opening the power supply connection of each of said electronic circuits; and said computing means comprising means for controlling said signalling means and said opening means in response to the power supply current to at least one of said electric circuits having a magnitude outside a given range.

2. An electropneumatic converter as in claim 1, wherein the electric motors and the displacement pump rotate in hydrodynamic bearings.

3. An electropneumatic converter as in claim 1, wherein the electric motors are brushless DC motors.

4. An electropneumatic converter as in claim 2, wherein the electric motors are brushless DC motors.

* * * * *